US00PP27298P3

(12) United States Plant Patent
Grosser

(10) Patent No.: US PP27,298 P3
(45) Date of Patent: Oct. 25, 2016

(54) CITRUS ROOTSTOCK NAMED 'UFR-5'

(50) Latin Name: *Citrus reticulata/Citrus paradisi+Citrus grandis×Citrus sinensis+Poncirus trifoliata*
Varietal Denomination: UFR-5

(71) Applicant: Florida Foundation Seed Producers, Inc., Marianna, FL (US)

(72) Inventor: Jude W. Grosser, Winter Haven, FL (US)

(73) Assignee: Florida Foundation Seed Products, Inc., Marianna, FL (US)

( * ) Notice: Subject to any disclaimer, the term of this patent is extended or adjusted under 35 U.S.C. 154(b) by 0 days.

(21) Appl. No.: 14/544,573

(22) Filed: Jan. 22, 2015

(65) Prior Publication Data

US 2015/0237783 P1 Aug. 20, 2015

Related U.S. Application Data

(60) Provisional application No. 61/942,574, filed on Feb. 20, 2014.

(51) Int. Cl.
*A01H 5/00* (2006.01)

(52) U.S. Cl.
USPC ..... Plt./201

(58) Field of Classification Search
USPC ..... Plt./201
See application file for complete search history.

(56) References Cited

U.S. PATENT DOCUMENTS

PP21,535 P2 11/2010 Grosser

OTHER PUBLICATIONS

PLUTO: Plant Variety Database, Jan. 13, 2015, citation for 'UFR-5'. 1 page.*
U.S. Appl. No. 14/544,424, filed Jan. 5, 2015, Grosser.
U.S. Appl. No. 14,544,425, filed Jan. 5, 2015, Grosser.
U.S. Appl. No. 14/544,423, filed Jan. 5, 2015, Grosser.
U.S. Appl. No. 14/544,427, filed Jan. 5, 2015, Grosser.
U.S. Appl. No. 14/544,571, filed Jan. 22, 2015, Grosser.
U.S. Appl. No. 14/544,572, filed Jan. 22, 2015, Grosser.
U.S. Appl. No. 14/545,063, filed Mar. 20, 2015, Grosser.
U.S. Appl. No. 14/544,570, filed Jan. 22, 2015, Grosser.
Grosser et al., "Protoplast fusion and citrus improvement," *Plant Breeding Reviews* 8:339-374, 1990.
Grosser et al., "Development of "tetrazyg" rootstocks tolerant of the diaprepes/phytophthora complex under greenhouse conditions," *Proc. Fla. State Hort. Soc.* 116:263-267, 2003.
Grosser et al., "Continued Development of Rootstocks Tolerant of the *Phytophthora*-Diaprepes Complex via Greenhouse Screening," *Proc. Fla. State Hort. Soc.* 120:103-109, 2007.
Grosser et al., "Protoplast fusion for production of tetraploids and triploids: Applications for scion and rootstock breeding in citrus," *Plant Cell Tissue Organ Culture* 104:343-357, 2011.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UFR-5' is a new and distinct allotetraploid citrus rootstock for tree size control and improved disease resistance. 'UFR-5' has shown a positive reaction to the Huanglongbing disease (HLB, or citrus greening disease) in multiple experimental field trials. Scion trees grafted on this rootstock show a reduced frequency of infection and reduced disease symptoms once infected as compared to commercial diploid rootstocks.

6 Drawing Sheets

Latin name of the genus and species of the plant claimed: *Citrus reticulata/Citrus paradisi+Citrus grandis×Citrus sinensis+Poncirus trifoliata.*

Variety denomination: 'UFR-5'.

BACKGROUND OF THE INVENTION

The present invention relates to a new and distinct variety of citrus rootstock named 'UFR-5'. The Plant Improvement Team in Lake Alfred, Fla. has pioneered the development and testing of allotetraploid citrus rootstocks. 'UFR-5' (identified as White #4 in field trials) is an allotetraploid zygotic hybrid derived from a conventional cross of two somatic hybrids previously produced by protoplast fusion. The somatic hybrid seed parent is 'Nova' mandarin hybrid+ 'Hirado Buntan' pummelo (zygotic seedling), and the somatic hybrid pollen parent is 'Succari' sweet orange+ 'Argentine' trifoliate orange.

BRIEF SUMMARY OF THE INVENTION

'UFR-5' was selected as a potential citrus rootstock on the basis of its positive reaction to Huanglongbing disease (HLB, or citrus greening disease) in multiple experimental field trials. Scion trees grafted onto this rootstock showed a reduced frequency of infection and reduced disease symptoms once infected when compared to other commercial diploid rootstocks. Although scion trees grafted onto 'UFR-5' grow off quickly, the trees remain small-medium in size, comparable to scion trees grafted onto 'Swingle' citrumelo rootstock. Scion trees are small in size when grown on flatwoods soils. 'UFR-5' is seedy and polyembryonic, making it suitable for standard nursery propagation practices for uniform liner production. 'UFR-5' has shown tolerance to *Diaprepes/Phytophthora* complex in greenhouse tests (Grosser et al., 2003). 'UFR-5' produces high quality sweet orange fruit. Long-term performance of trees on this rootstock selection is unknown. Yield and fruit quality data is limited, but 3 years of data from young trees (the St. Helena project, see Table 1) indicates good productivity and fruit quality. Tolerance to citrus blight is also unknown, but under investigation. True-to typeness of UFR-5 through asexual reproduction was demonstrated by topworking a 'Swingle' citrumelo rootstock in Osceola county, Fla. Seeds from this tree and the original tree are predominantly of nucellar origin and produce true-to-type seedlings.

TABLE 1

Rootstock Data from 5-year old trees in the St. Helena trial - Dundee, FL.

| | | | Lbs Solids/Box | |
|---|---|---|---|---|
| Scion | Type | Rootstock | 2012 | 2013 |
| VALQUARIUS | Som. Hyb. | 'UFR-6' | 5.64 | 5.43 |
| VERNIA | Som. Hyb. | 'UFR-6' | 5.67 | 6.01 |
| VALQUARIUS | Tetrazyg | 'UFR-1' | 5.5 | 4.87 |
| VERNIA | Tetrazyg | 'UFR-1' | 5.61 | 6.28 |
| VERNIA | Tetrazyg | 'UFR-2' | 5.47 | 5.93 |
| VALQUARIUS | Tetrazyg | 'UFR-2' | 4.57 | 5.37 |
| VALQUARIUS | Tetrazyg | 'UFR-3' | 4.84 | 5.05 |
| VERNIA | Tetrazyg | 'UFR-3' | 5.46 | 5.82 |
| VERNIA | Tetrazyg | 'UFR-4' | 5.79 | 6.07 |
| VALQUARIUS | Tetrazyg | 'UFR-4' | 4.65 | 5.07 |
| VALQUARIUS | Tetrazyg | 'UFR-5' | 5.76 | 5.72 |
| VERNIA | Tetrazyg | 'UFR-5' | 5.89 | 5.34 |
| VALQUARIUS | Diploid | FG 1731 | 5.83 | 6.81 |
| VALQUARIUS | Diploid | FG 1733 | 5.12 | 5.63 |
| VERNIA | Diploid | SWINGLE* | 5.11 | 5.79 |
| VALQUARIUS | Diploid | SWINGLE* | NS | 5.61 |
| VERNIA | Diploid | CLEO* | 4.79 | 5.51 |
| VALQUARIUS | Diploid | CLEO* | NS | 5.21 |
| VERNIA | Diploid | R. LEMON* | 3.67 | na |
| VALQUARIUS | Diploid | VOLK* | NS | 4.12 |
| VERNIA | Diploid | VOLK* | 3.6 | 4.73 |
| VALQUARIUS | Diploid | KUHARSKE* | NS | 5.75 |
| VERNIA | Diploid | KUHARSKE* | 4.34 | 5.83 |

| | Yield Boxes/Tree | | | Cumulative |
|---|---|---|---|---|
| Scion | 2011 (35 mo.) | 2012 (47 mo.) | 2013 (59 mo.) | Yield (Boxes) |
| VALQUARIUS | 0.5 | 0.78 | 1.94 | 3.22 |
| VERNIA | 0.4 | 0.63 | 1.41 | 2.44 |
| VALQUARIUS | NS | 0.72 | 2.23 | 2.95 |
| VERNIA | 0.31 | 0.67 | 1.33 | 2.31 |
| VERNIA | 0.35 | 0.25 | 1.38 | 1.98 |
| VALQUARIUS | NS | 0.75 | 1.73 | 2.48 |
| VALQUARIUS | NS | 0.81 | 1.97 | 2.78 |
| VERNIA | 0.37 | 0.38 | 1.82 | 2.57 |
| VERNIA | 0.54 | 0.71 | 1.73 | 2.98 |
| VALQUARIUS | NS | 0.65 | 1.59 | 2.64 |
| VALQUARIUS | 0.33 | 0.56 | 1.80 | 2.69 |
| VERNIA | 0.42 | 0.25 | 1.93 | 2.60 |
| VALQUARIUS | NS | 0.68 | 2.20 | 2.88 |
| VALQUARIUS | NS | 0.67 | 2.77 | 3.44 |
| VERNIA | 0.33 | 0.85 | 1.08 | 2.26 |
| VALQUARIUS | NS | NS | 1.50 | 1.50 |
| VERNIA | NS | 0.50 | 0.83 | 1.33 |
| VALQUARIUS | NS | NS | 1.7 | 1.7 |
| VERNIA | NS | 0.78 | na | 0.78 |
| VALQUARIUS | NS | NS | 2.58 | 2.58 |
| VERNIA | 0.4 | 1.13 | 0.83 | 2.36 |
| VALQUARIUS | NS | NS | 2.2 | 2.2 |
| VERNIA | 0.15 | 0.75 | 1.08 | 1.98 |

NS - not significant fruit; na - data not available; * - control commercial rootstock
One box contains approximately 90 lbs. fruit.

BRIEF DESCRIPTION OF THE DRAWINGS

'UFR-5' is illustrated by the accompanying photographs, which show the tree's form, foliage, and fruit. The colors shown are as true as can be reasonably obtained by conventional photographic procedures. The photographs are of a tree approximately 11 years old. All figures were taken in the fall of 2013.

DETAILED BOTANICAL DESCRIPTION

Figure 1:
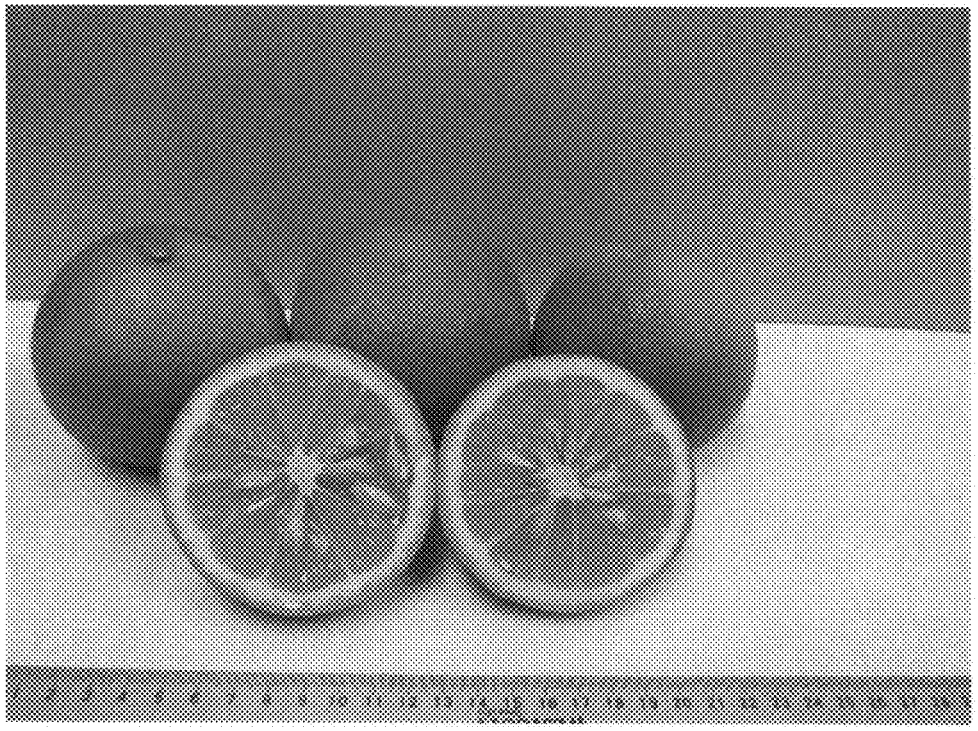
FIG. 1.—Shows a close-up of the nearly mature fruits with the rind and cross-sectional view of the fruit when cut in the center.
Figure 2:
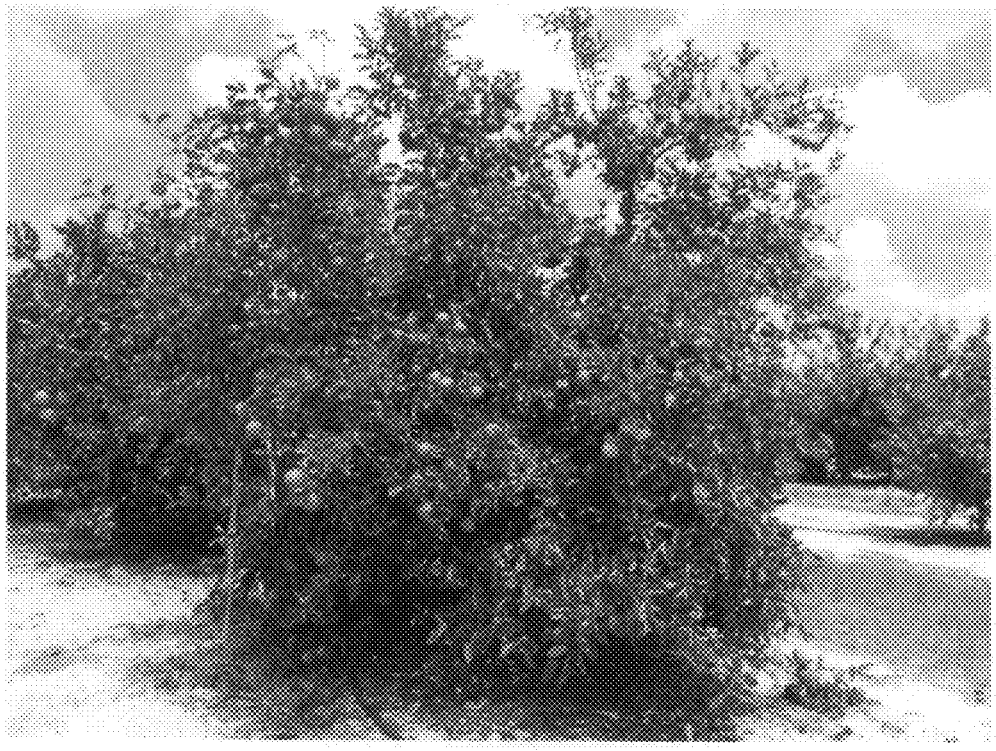
FIG. 2.—Shows the overall mature plant growth habit.
Figure 3:
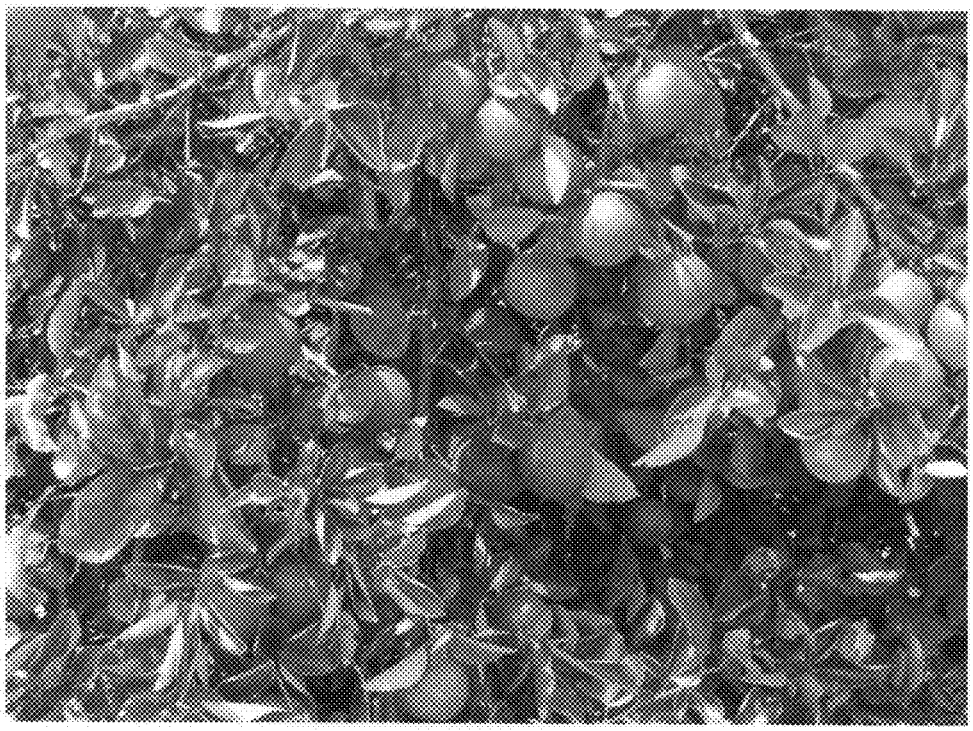
FIG. 3.—Shows nearly mature fruits hanging on the tree.
Figure 4:
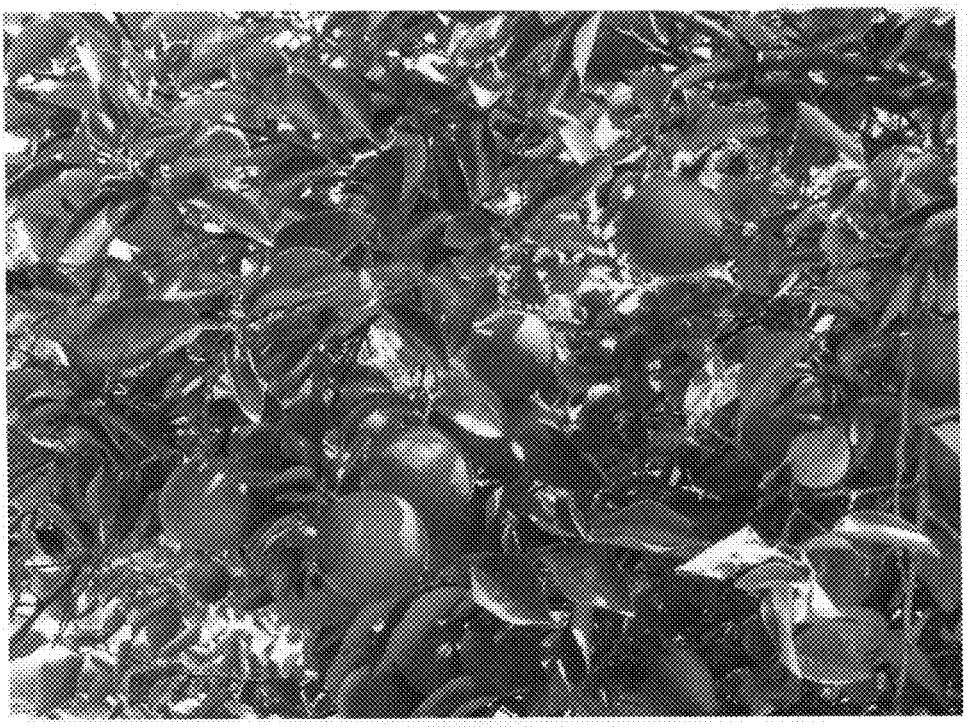
FIG. 4.—Shows leaves and nearly mature fruits.
Figure 5:
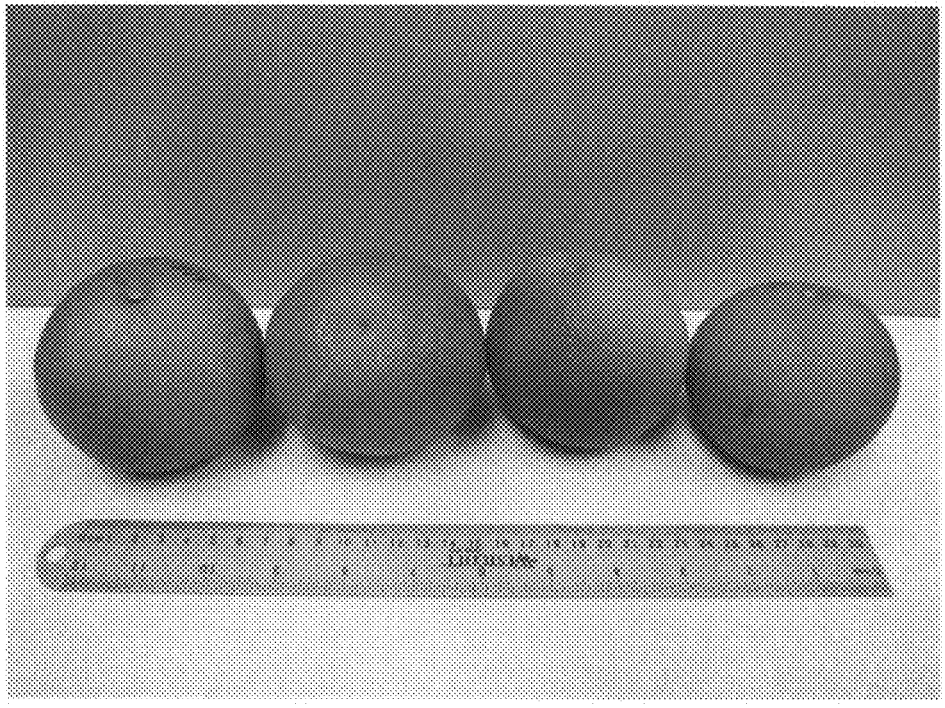
FIG. 5.—Shows a close-up of nearly mature fruits.
Figure 6:
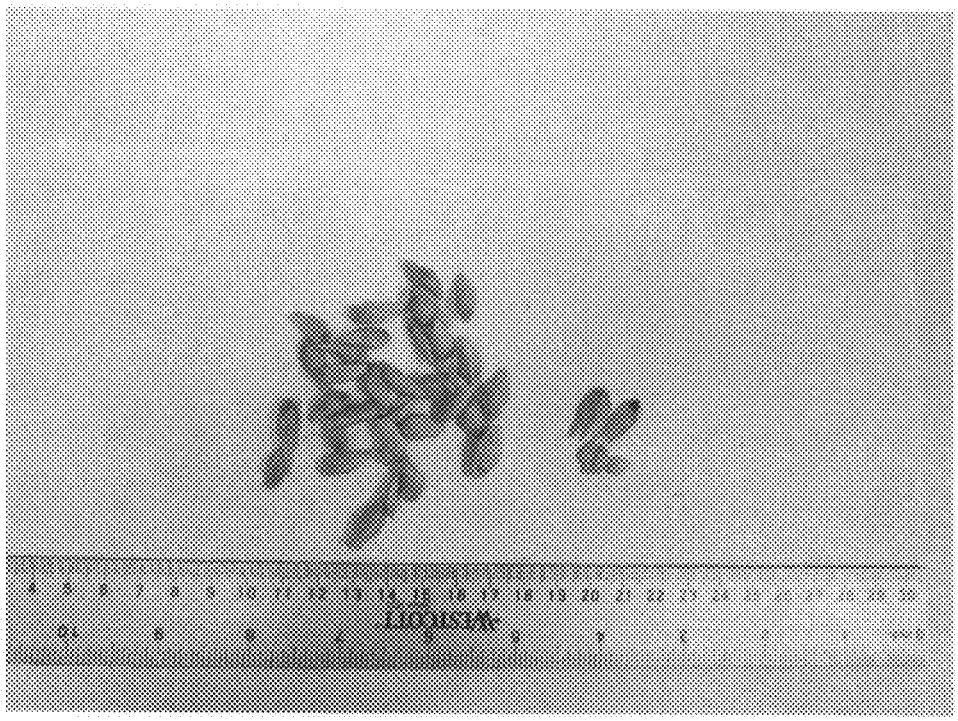
FIG. 6.—Shows a close-up of seeds from nearly mature fruit.

The following detailed description sets forth the distinctive characteristics of 'UFR-5'. The colors (except those in common terms) are described from The R.H.S. Colour Chart published by The Royal Horticultural Society in London (second edition), in association with the Flower Council of Holland.

Phenotypic Description of *Citrus reticulata/Citrus paradisi+Citrus grandis×Citrus sinensis+Poncirus trifoliata* 'UFR-5'

Classification:

*Botanical*.—[Complex allotetraploid hybrid rootstock ('Clementine' mandarin×'Orlando' tangelo) *Citrus reticulata×Citrus paradisi)+Citrus grandis]×[Citrus sinensis+Poncirus trifoliata* (trifoliate orange)].

*Common name*.—Complex allotetraploid hybrid rootstock.

Parentage:

*Female parent*.—'Nova' mandarin+'Hirado Buntan' pummelo (zygotic seedling) somatic hybrid (unpatented).

*Male parent*.—'Succari' sweet orange+'Argentine' trifoliate orange; somatic hybrid (unpatented).

Tree:

*Ploidy*.—Tetraploid.

*Size*.—Medium-large.

*Height*.—4.62 meters.

*Tree spread*.—3.8 to 4.0 meters.

*Vigor*.—Moderately vigorous.

*Density*.—Canopies are moderately dense.

*Form*.—The tree is round-shaped with lateral and upright branches.

*Growth habit*.—Both upright and lateral growth with a medium angle.

Trunk:

*Trunk diameter*.—21 cm in diameter at 30 cm above the ground on a 16-year-old tree.

*Trunk texture*.—Rough.

*Trunk bark color*.—RHS 198A (greyed-green); irregularly striated with RHS 197A (greyed-green).

Branches:

*Crotch angle*.—First crotch forms 40- to 45-degree angle, middle crotch forms a 85-degree angle.

*Branch length*.—Branch reaches 4.0 meters from the first crotch to the tip of the branch.

*Branch texture*.—Relatively rough with small thorns or spines.

*Branch color* (*shoots from previous flush, hardened and 4 to 5 mm in diameter*).—RHS N137A (green).

Leaves:

*Size* (*lamina average*).—Length: 106.7 mm. Width: 70 mm. L/W ratio: 1.51.

*Thickness*.—Thicker than average diploid citrus rootstock hybrids.

*Type*.—Simple.

*Shape*.—Elliptical.

*Apex*.—Retuse.

*Base*.—Acute to sub-obtuse.

*Margin*.—Entire and slightly undulate.

*Surface*.—Upper surface: Glabrous. Lower surface: Medium veins that are pinnately netted.

*Color*.—Upper surface (adaxial): RHS 137A (green). Lower surface (abaxial): RHS 146A (yellow-green).

*Petiole*.—Shape: Brevipetiolate (shorter than leaf lamina); junction between petiole and lamina is articulate. Width (petiole wing): Narrow, with obvious medium broaden wing. Shape (petiole wing): Obovate. Length: 13.5 to 19.5 mm. Width: 4 to 9 mm. Color: RHS 137A (green).

Flowers and flower buds:

*Type*.—Hermaphrodite.

*Bearing*.—Flowers grow from leaf axillaries and leaf terminals singly and in small clusters; most single flowers grow from leaf axillaries.

*Flower diameter*.—Fully open flower with an average diameter of 36.8 to 38.2 mm.

*Flower depth*.—Typical flower with average depth of 19.1 mm.

*Flower blooming period*.—First bloom observed Mar. 2, 2016. Full bloom observed Mar. 12, 2016.

*Flower bud*.—Initial visible flower bud size: Length: 2.8 mm in length. Diameter: 3.1 mm in diameter. Mature flower bud size: Length: 17.3 mm in length. Diameter: 10.0 mm in diameter. Color: RHS 144C (yellow-green) for initial visible flower bud; RHS NN155D (white) for mature flower bud with RHS 150D (yellow-green) spots distributed at tip of the flower bud. Shape: Initial visible flower bud has a round ball shape; mature flower bud has an elongated olive shape.

*Flower petals*.—Shape: Flat, spatula-shaped. Apex shape: Smooth, acute-shaped. Base shape: Even obtuse. Color: Upper surface RHS NN155D (white); lower surface RHS NN150D (white) with RHS 150D (yellow-green) spots distributed toward to the petal apex. Length: 19.2 to 23.6 mm. Width: 10.3 to 11.0 mm. Thickness: 0.9 to 1.1 mm. Texture: Medium soft, smooth. Margin: Smooth.

*Flower sepal*.—Number: 5 per flower. Shape: Delta-shaped with an acute angle at the apex. Length: 3.8 mm. Width: 4.2 mm. Apex shape: Triangle-shaped. Margin: Smooth. Color: Upper surface RHS 154C (yellow-green); lower surface RHS 144D (yellow-green).

*Fragrance*.—Fragrant/Moderately fragrant.

*Flower pedicel*.—Length: 4.5 mm to 4.9 mm. Diameter: 1.3 mm to 1.6 mm. Color: RHS 144D (yellow-green).

*Reproductive organs*.—Fertility: Appears self-fertile. Pollen amount: Abundant/Moderate amount. Pollen color (general): Bright-yellow. Ovary shape: Oval-shaped.

Fruit:

*Size*.—Uniform.

*Height*.—79.3 to 81.2 mm on average.

*Width*.—82 to 86.5 mm on average.

*Average weight* (*per individual fruit*).—263 grams.

*Shape*.—Round and earth shaped.

*Shape* (*cross-section*).—Round.

*Apex*.—Truncated with slight dent.

*Apex cavity diameter*.—N/A.

*Base cavity diameter*.—5.4 to 5.7 mm.

*Base*.—No neck.

*Harvesting*.—Fruit can be harvested from October through December in Florida.

*Fruit stem* (*short stem connecting the fruit*).—Length: 11.6 mm. Diameter: 5.1 mm. Color: RHS 198A (greyed-green) with RHS 137C (grey-green) strip.

Rind:

*Adherence*.—Adherence between albedo (mesocarp) and flesh (endocarp) is medium. The adherence is evenly distributed from base to apex.

*Thickness*.—3.4 to 4.8 mm on average.

*Texture*.—Smooth.

*Color*.—Flavedo (epicarp): Ranges between RHS 151B (yellow-green) to RHS 151A (yellow-green). Albedo (mesocarp): RHS 157D (green-white).

*Stylar end*.—Closed.

*Rind oil cell density*.—62 oil cells/square cm.

Flesh:

*Number of segments*.—Between 7 and 8 segments per fruit on average.

*Segment walls*.—Firm with sufficient strength to maintain integrity as separated.

*Juice*.—Abundant.

*Color*.—Uniformly RHS 11C (greyed-yellow).

*Texture*.—Medium soft.

*Vesicles*.—Length: Arranged from 11.5 to 12.2 mm on average. Diameter (thickness): 3.8 to 4.2 mm on average.

*Eating quality*.—N/A.

*Juice index*.—.

*Soluble solids* (*average*).—10 Brix.

Seeds:

*Type*.—Polyembryonic.

*Number*.—Ranges from 24 to 34.

*Shape*.—Seed shapes are not uniform. Normal seeds are mostly ventricose/swollen-shaped and clavate club shaped.

*Size*.—Length: 17 to 18.2 mm. Width: 8 to 8.9 mm.

*Seed coat color*.—Outer Surface: RHS 155B (white) and wrinkled. Inner surface: RHS 146B (greyed-orange). Cotyledon color: RHS 145D (yellow-green).

Resistance to disease: 'UFR-5' rootstock was selected on the basis of its positive reaction to HLB disease (huanglongbing or citrus greening disease) in multiple field trials. Trees on this rootstock show a reduced frequency of infection and reduced disease symptoms once infected as compared to commercial diploid rootstocks.

What is claimed is:

1. A new and distinct citrus rootstock cultivar as illustrated and described herein.

* * * * *